(12) United States Patent
Duval

(10) Patent No.: US 6,346,616 B1
(45) Date of Patent: Feb. 12, 2002

(54) CHLORO-, HYDROXY- AND ALKOXYSILANE DERIVATIVES OF POLYSACCHARIDES OR OLIGOSACCHARIDES, POLYMERIZABLE AND CROSS-LINKABLE, THEIR SYNTHESIS AND THEIR USE AS SOURCES OF NOVEL SUPPORT MATERIALS

(75) Inventor: Raphaël Duval, Notre Dame de Gravenchon (FR)

(73) Assignees: Institut Francais du Petrole, Rueil Malmaison; Chiralsep S.A.R.L., La Frenaye, both of (FR)

( * ) Notice: Subject to any disclaimer, the term of this patent is extended or adjusted under 35 U.S.C. 154(b) by 0 days.

(21) Appl. No.: 09/394,868

(22) Filed: Sep. 13, 1999

(30) Foreign Application Priority Data

Sep. 11, 1998 (FR) .............................. 98 11377

(51) Int. Cl.[7] .............................. C07H 23/00

(52) U.S. Cl. ............ 536/123.1; 536/56; 210/635; 210/730

(58) Field of Search ............... 536/56, 123.1; 210/730, 635

(56) References Cited

U.S. PATENT DOCUMENTS 5,032,682 A * 7/1991 Sau
5,811,532 A * 9/1998 House

OTHER PUBLICATIONS

Patent Abstract of Japan, Tanaka Minoru, Fixation of Cyclodextrin, Pub. No. 05271307.

* cited by examiner

Primary Examiner—Margaret G. Moore
Assistant Examiner—Marc S. Zimmer
(74) Attorney, Agent, or Firm—Millen, White, Zelano & Branigan, P.C.

(57) ABSTRACT

There are described chloro-, hydroxy- and alkoxysilane derivatives of polysaccharides or oligosaccharides as novel compounds which are polymerizable and cross-linkable, and a method for obtaining them; novel support materials obtained from said derivatives and containing said silane derivatives of polysaccharides or oligosaccharides chemically grafted by a covalent bond with the support and polymerized and cross-linked in a three-dimensional network and a method for obtaining them; as well as the use of said material supports in separation or in preparation of enantiomers, through employment in gaseous, liquid or supercritical chromatography, by electrophoresis, electrochromatography or by percolation processes through membranes containing said support materials.

22 Claims, No Drawings

CHLORO-, HYDROXY- AND ALKOXYSILANE DERIVATIVES OF POLYSACCHARIDES OR OLIGOSACCHARIDES, POLYMERIZABLE AND CROSS-LINKABLE, THEIR SYNTHESIS AND THEIR USE AS SOURCES OF NOVEL SUPPORT MATERIALS

The invention relates to chloro-, hydroxy- and alkoxysilane derivatives of polysaccharides or oligosaccharides as novel compounds which are polymerizable and cross-linkable, and a method for obtaining them.

The invention also relates to novel material supports obtained from said derivatives and containing said silane derivatives of polysaccharides or oligosaccharides chemically grafted by a covalent bond with the support and polymerizable and cross-linkable in a three-dimensional network. The invention also relates to a method for obtaining said support materials.

The invention also relates to the use of said support materials in separation or in preparation of enantiomers, through employment in gaseous, liquid or supercritical chromatography, by electrophoresis, electrochromatography or by percolation processes through membranes containing said support materials.

The separation of enantiomers has been an expanding field for some twenty years, at both the preparation and analysis level. This is true in particular of pharmacy applications, where legislation requires a separate study of the optical isomers of any compound included in the composition of a medicament. Substituted polysaccharides have the subject of numerous studies, and celluloses deposited physically on a silica gel support are marketed. However, such compounds have the disadvantage of being most often soluble in organic polar solvents, which singularly limits their use.

Recent solutions have been provided to the problem of solubilization, by establishing covalent bonds between the substituted polysaccharide and the support. Kimata et al. published their results (Analytical Methods and Instrumentation, Vol. 1, 23–29 (1993)) on a chiral stationary phase based on cellulose-tris-2,3,6-(4-vinyl benzoate) deposited on silica gel then polymerized on the support.

The chromatographic data obtained with two racemic test mixtures are as follows:

|  | Deposited support | | Deposited and polymerized support | |
| --- | --- | --- | --- | --- |
|  | Stilbene oxide | 1-(1-naphthyl ethanol) | Stilbene oxide | 1-(1-naphthyl ethanol) |
| k'1 | 1.08 | 2.15 | 1.04 | 1.47 |
| k'2 | 1.66 | 2.84 | 1.44 | 1.80 |
| α | 1.54 | 1.32 | 1.39 | 1.22 |
| $R_s$ | 3.63 | 2.34 | 3.82 | 1.44 | where k'1 and k'2 are the capacity factors, that is to say if i=1 or 2, $k'_i=(t_{Ri}-t_o)/t_o$, $t_{Ri}$ being the retention time of the compound i and $t_o$ the dead time;

α is the selectivity factor: $\alpha=(t_{R2}-t_o)/(t_{R1}-t_o)=k'2/k'1$ $R_s$ is the resolution factor:

$$R_s = \frac{1}{4}\left(\frac{(\alpha-1)}{(\alpha)}\right)\left(\frac{(k'2)}{(1+k'2)}\right)(N)^{1/2}$$

N being the number of plates determined on the basis of chromatographic values measured on chromatogram.

A systematic decline in the obtained selectivity factors can be seen between the deposited support and the deposited and polymerized support: 10% less on trans-stilbene oxide (α changes from 1.54 to 1.39) and 7.5% less for 1-(1-naphthyl)ethanol (α changes from 1.32 to 1.22).

This phenomenon could be explained by a partial solubility of the polymerized support because of an incomplete polymerization due to a low reactivity of the vinyl benzoate group in the reaction conditions employed.

On the other hand, Kimata et al. offer no example of separation in a pure polar solvent (patent or publication).

Okamoto et al. have described (EP-B-0 155 637) polymers chemically bound to silica gel. They describe in particular the grafting of cellulose tris-2,3,6-phenyl carbamate onto silica gel via a tritylated intermediate then the realization of the covalent bond, between the silica gel and the partially derived polysaccharide carbamate, by action of a diisocyanate.

The results of the elemental analyses carried out at various synthesis stages are as follows (EP-B-0 155 637, page 8 to page 9, line 33).

|  |  | C % | H % | N % |
| --- | --- | --- | --- | --- |
| 1. | Cellulose trityl deposited on silica | 15.40 | 1.23 | 0.09 |
| 2. | Detriylated cellulose deposited on silica | 3.61 | 0.60 | — |
| 3. | Cellulose bound to the silica by toluene 2,4 diisocyanate | — | — | — |
| 4. | Phenyl carbamate cellulose bound to the silica and washed with THF/chloroform | 3.23 | 0.27 | 0.45 |

The drop in the rate of grafting between the cellulose deposited on silica (2) and the cellulose phenyl carbamate bound to the silica (4) is substantial knowing that the rate of (4) calculated according to (2) is of the order of 14% carbon. The loss of hydrocarbon groups can thus be estimated at 80% from the realization of the covalent bond, between the cellulose and the silica, by the diisocyanate arm followed by the derivation of the OHs with phenyl isocyanate and the final washing with chloroform. No example of separation in polar solvents is given for the support obtained.

Okamoto et al. have described (JP-A-06-206 893) an oligosaccharide chemically bound to silica gel via an amine-reduced imine function. The amylose is then regenerated by the chemoenzymatic route from this oligosaccharide. The available hydroxyl functions are then derived as carbamate functions. No example of separation in a pure polar solvent is given.

On the other hand, it is beneficial to work with a substantial column overload for preparatory applications. The possibility of using 100% of the chiral material in the form of balls of pure polymer of substituted polysaccharides, instead of depositing them physically on a support, has proved effective in increasing the mass yields of preparatory chiral chromatography processes. Thus patents EP-B-348 352, and EP-B-316 270 and WO-A-96/27 639 relate to the realization of cellulose balls for the separation of optical isomers.

However, the pure polymer balls are soluble in polar solvents such as halogenated solvents, tetrahydrofuran, dioxan, etc. It is thus impossible to use these pure solvents or mixtures with high proportions of the latter to realize separations of isomers.

In order to overcome this drawback, Francotte et al. described the polymerization by is radiation of derived polysaccharides (WO-A-96/27 615).

However, the rate of polymerization seems difficult to control in such a process, cross-linking by photochemical process preferentially occurring at the surface of the polymer ball, the rays being unable to penetrate inside the ball. No example of separation is given in a pure polymer.

Francotte et al. have also described in international application WO-A-97/04 011 the chemical cross-linking of carbamates and esters of polysaccharides not containing a polymerizable group. According to the author, crosslinking took place in the presence of a radical polymerization initiator. The reaction mechanism and the structure of the products obtained are not described. No example of separation in a pure polar solvent is given.

Lange at al. have described (U.S. Pat. No. 5,274,167) the polymerization of optically active derivatives of methacrylic acid, the structure of the support not being explained. No example of separation in a pure polar solvent is given.

Minguillon et al. have described the synthesis of partially derived cellulose carbamates with an undecenoyl chloride. However, the structure of the support is not explained (J. of Chromatog. A 728 (1996), 407–414 and 415–422).

Oliveros et al. (WO-A-95/18 833) describe polysaccharide derivatives containing an ethylene radical and deposited on a silica gel support containing vinyl groups then polymerized. No example of separation is given with a pure polar solvent.

The present invention relates to the preparation of novel silane derivatives of polysaccharides or oligosaccharides containing chlorosilane, hydroxysilane or alkoxysilane functions which are easily polymerizable and cross-linkable in a three-dimensional network. Said derivatives are used for obtaining novel support materials containing them and characterized in that are bound by a chemical covalent bond to the support and concomitantly polymerized and cross-linked in a three-dimensional network. Said support materials are used for the separation of enantiomers by chromatography, in particular in pure polar solvents such as chloroform, dichloromethane, tetrahydrofuran, acetone, toluene, ethyl acetate or any other polar organic solvent.

The present invention also relates to a method for obtaining silane derivatives of polysaccharides or oligosaccharides containing chlorosilane, hydroxysilane or alkoxysilane groups. The subsequent obtaining of support materials is realized by physically depositing said silane derivatives of polysaccharides obtained, on a support and reacting the chlorosilane, hydroxysilane or alkoxysilane functions with said support in order to realize chemical covalent bonds of Si—O-(support) type with polymerization and concomitant three-dimensional cross-linking of the silane derivative of polysaccharide by creation of chemical covalent bonds of Si—O—Si— type between the chains of the polysaccharide derivative. The method also includes the separation and preparation of enantiomers by employing said support materials in liquid, gas or supercritical chromatography processes, in organic synthesis or in percolation processes through membranes containing said support materials.

The support materials according to the invention possess a stability and total insolubility in polar solvents such as tetrahydrofuran, chloroform, dichloromethane, acetonitrile, toluene or ethyl acetate, as well as in any other organic solvent such as ethers for example. The stability and insolubility of said support materials is effective up to high temperature (greater than 100° C.).

The chlorosilane, hydroxysilane or alkoxysilane derivatives of polysaccharides according to the invention are constituted by linkages of osidic chiral units forming linear, branched or cyclic chains and which can be represented by one of the general formulae below:

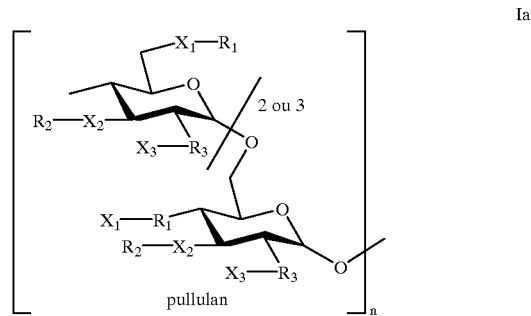

Ia

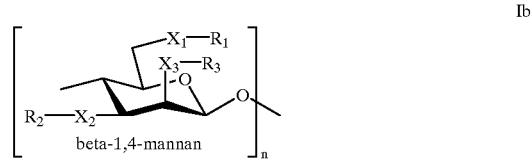

Ib

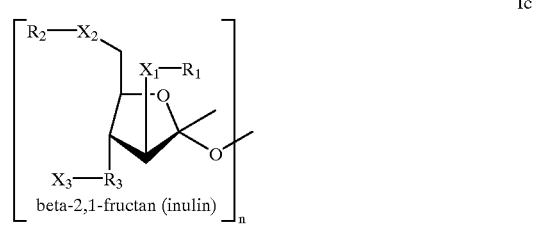

Ic

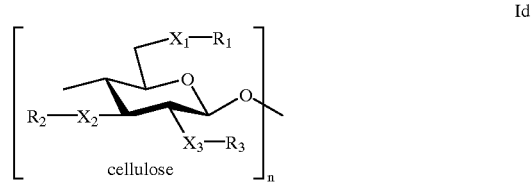

Id

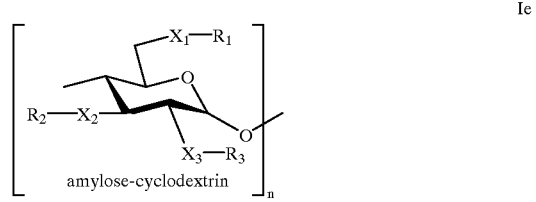

Ie

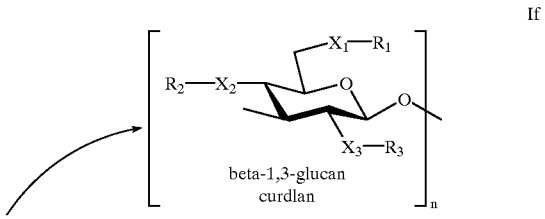

If

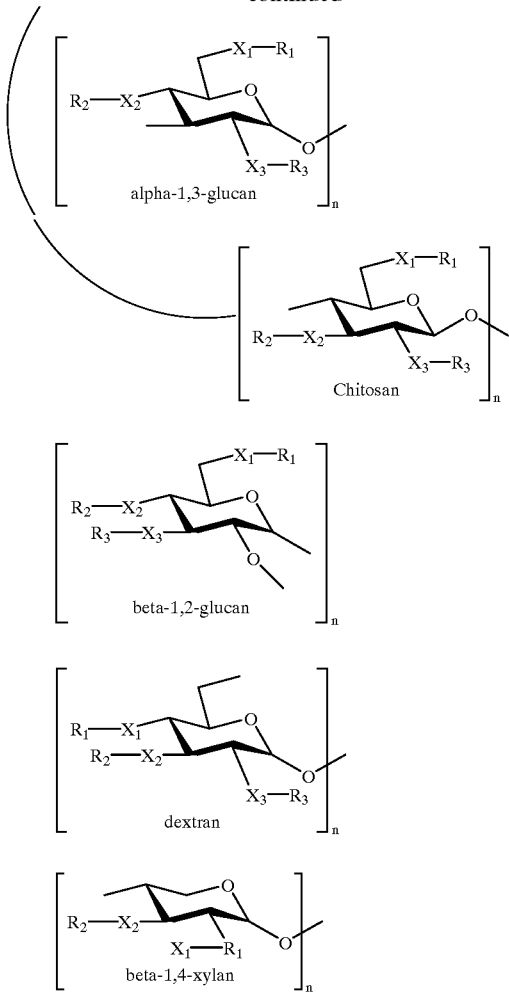

in which:
  a) the symbols $X_1$, $X_2$ and $X_3$, identical or different, each represent an oxygen atom or the —NH group;
  b) each of the symbols $R_1$, $R_2$ and $R_3$ independently represents:
    a chlorosilane, hydroxysilane or alkoxysilane radical of general formula $[(X)_3Si—W—CH_2—CH_2]_mA—Y—$ (II) in which m is a non-zero integer at most equal to 5, Y is a single bond, an —NH—CO— group, an —NH—CS— group or a —CO— group, A represents a single bond, a linear or branched alkylene radical having 1 to 21 carbon atoms, an arylene radical having 6 to 18 carbon atoms or an aralkylene radical having 7 to 40 carbon atoms, W represents a single bond or the —CH$_2$—CH$_2$—CH$_2$—S— group and X represents a halogen, a hydroxyl or an alkoxy;
    or a radical having the formula $A_2—A_1—CX_4—$ (III) in which $X_4$ represents an oxygen or sulphur atom, $A_1$ represents a single bond or an —NH— group and $A_2$ represents an aryl radical having from 6 to 24 carbon atoms, an aralkyl radical having from 7 to 36 carbon atoms or an alkylaryl radical having from 7 to 18 carbon atoms;
    or a hydrogen atom or an NO$_2$ group; n being an integer between 5 and 20000,
  it being understood that, in each osidic chiral unit (Ia) to (Ik), at least one of the symbols $X_1$, $X_2$ and $X_3$ represents an oxygen atom, and that, in at least part of the osidic units constituting the polysaccharide derivative, at least one of the symbols $R_1$, $R_2$ and $R_3$ represents a radical of general formula (II) and at least one of the symbols $R_1$, $R_2$ and $R_3$ represents a radical of general formula (III).

The arylene or aryl radicals contained respectively in the radicals of general formulae (II) and (III) may optionally be substituted by one or more atoms or radicals, identical or different, chosen from halogen atoms, alkyl radicals containing from 1 to 4 carbon atoms, alkoxy radicals containing from 1 to 4 carbon, atoms and nitro groups. The arylene radicals contained in the radicals of general formula (II) are, preferably, phenylene radicals or naphthylene radicals, optionally substituted by one or more atoms or radicals, identical or different, chosen from halogen atoms and alkyl radicals containing from 1 to 4 carbon atoms, alkoxy radicals containing from 1 to 4 carbon atoms and nitro groups. The aryl radicals contained in the radicals of general formula (III) are, preferably, phenyl radicals or naphthyl radicals, optionally substituted by one or more atoms or radicals, identical or different, chosen from halogen atoms, alkyl radicals containing from 1 to 4 carbon atoms, alkyloxy radicals containing from 1 to 4 carbon atoms and nitro groups, Generally, the silane derivatives of polysaccharides according to the invention have a degree of polymerization between 5 and 20000 and preferably between 10 and 500.

Generally, the silane derivatives of polysaccharides according to the invention contain from 0.05 to 3, preferably from 0.05 to 2.95 groups of general formula (II) per structural unit of general formula (Ia) to (Ik), and from 0 to 2.95, preferably from 0.05 to 2.95 groups of general formula (III) per structural unit of general formula (Ia) to (Ik).

Generally, the polysaccharide derivatives according to the invention derive from amylose, cellulose, chitosan, α, β or γ cyclodextrins and dextran.

According to the invention, the silane derivatives of polysaccharides can be obtained by synthesis in two or three stages, where a reaction is carried out successively on a polysaccharide:

in stage 1, of a compound of general formula:

$$(CH_2=CH)_mA—Y_1 \qquad (IV)$$

in which R, m and A are defined as previously and $Y_1$ represents a halogen atom (chlorine, bromine), an —N=C=O group or —N=C=S group or a —CO—Z— group in which Z represents a halogen atom (chlorine, bromine) in order to introduce an ethylene radical, subsequently modified in stage 3 into chlorosilane, hydroxysilane or alkoxysilane;

in an optional stage 2, an isocyanate or an isothiocyanate of general formula:

$$A_2—A_1—N=C=X_5 \qquad (V)$$

in which $A_2$ and $A_1$ are defined as previously and $X_5$ represents an oxygen or sulphur atom
or a compound of general formula:

$$A_2—A_1—CO—Z_1 \qquad (VI)$$

in which $A_2$ and $A_1$ are defined as previously and $Z_1$ represents a halogen atom (chlorine, bromine) in order to introduce a radical of general formula (III);

and, in stage 3, a compound of general formula:

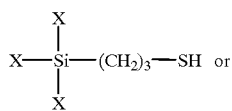

(VII)

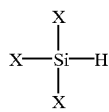

(VIII)

in which X is defined as previously in order to introduce a compound of general formula (II).

According to the invention, the introduction of the radicals of general formula (II) and optionally (III) takes place under the conditions customarily used for preparing an ether, an ester, an amide, a carbamate, a thiocarbamate, a urea or a thiourea, starting from the corresponding alcohol or amine.

Stage 1 and stage 2 are generally implemented in an organic solvent with a high boiling point, such as toluene, in the presence of an organic base such as pyridine or triethylamine. In the case where the compound of formula (IV) or (V) is an isocyanate, it is generally preferable to use a catalyst to encourage the kinetics of the reaction, dibutyltin dilaurate being preferred.

Obtaining the radicals of general formula (II) in stage 3 requires the reaction of compounds of formulae (VII) and (VIII) on the ethylene double bonds of the polysaccharides modified in stage 1 by the compounds of general formula (IV).

In stage 3, a distinction should be drawn in the procedure implemented as to whether a compound of formula (VII) or (VIII) is reacted.

In the first case a compound of formula (VII) is reacted.

The anti-Markovnikov addition reaction of thiol functions on ethylene double bonds, in the presence of a free radical initiator, which leads to the formation of thioether bonds is known per se. For example, Rosini and colleagues described the immobilization of cinchona alkaloids via a thioether bond in Tetrahedron Lett. 26, 3361–3364, 1985. More recently, Tambute and colleagues described the immobilization of tyrosine derivatives using the same technique in New J. Chem. 13 625–637, 1989. Even more recently, Caude and colleagues published the results of their work and showed the advantage of a covalent thioether bond in terms of chemical stability in J. Chromatogr. 550, 357–382, 1991.

Among the compounds of formula (VIII) the generally preferred product is the compound of formula:

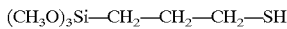

or γ-mercaptopropyltrimethoxysilane, which is available commercially.

This compound is used in the presence of compounds obtained after realization of stages 1 and 2 or stage 1, in an organic solvent, the preferred organic solvents being toluene, tetrahydrofuran and chloroform. A free radical initiator is added to the reaction medium, such as benzoyl peroxide for example.

In a second case a compound of formula (VIII) is reacted in stage 3.

The hydrosilylation of ethylene double bonds by hydrogenosilanes is known per se and used to create silicon-carbon bonds. For example, Stuurman, H. W., in Chromatopgraphia, Vol. 25, no. 4, April 1988, pp. 265 to 271, has described the separation of enantiomers through the use of a stationary phase based on hydrosilylated quinine bound to silica gel by a covalent bond.

Among the compounds of formula (VIII) the two products which are generally preferred are the compounds of formula $(C_2H_5O)_3SiH$ (triethoxysilane) and $Cl_3SiH$ (trichlorosilane), which are available commercially.

The triethoxysilane or trichlorosilane is used in the presence of compounds obtained after the realization of stages 1 and 2, or stage 1, in an organic solvent, the preferred solvents being toluene, dioxan or chloroform. A metal complex is generally used as catalyst. The preferred metal complexes are based on rhodium or platinum, such as hexachloroplatinic acid.

The invention also relates to support materials containing silane derivatives of polysaccharides of general formulae (Ia) to (Ik) and the chlorosilanes, hydroxysilanes and alkoxysilanes of which contained in the radicals of formula (II) were reacted with a support in order to obtain compounds of general formula (IXa) or (IXb) or (XII) hereafter and concomitantly reacted with themselves in order to create covalent bonds contained in formulae (IXc), (IXd), (XIII) or (XIV), hereafter.

The simultaneous employment of a reaction of silane derivatives of polysaccharides with a support and between them allows the creation of a three-dimensional network of silane derivatives bound in a covalent fashion to a support.

The difficulty of representing a support material according to the invention is obvious. Formula (IX) hereafter represents one of the possible variants of the set of formulae (IXa), (IXb), (IXc), (IXd), (XII), (XIII) and (XIV), when m is equal to 1, m being the symbol defined in formula (II).

The reactions employed are the following:

reaction with support of chlorosilanes, hydroxysilanes and alkoxysilanes for the creation of ≡Si—O—(support) bonds;

creation of siloxane bonds ≡Si—O—Si≡ or disiloxane bonds

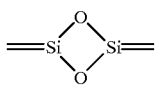

by reacting silane derivatives with each other.

The reaction of chlorosilanes, hydroxysilanes and alkoxysilanes with a support is known per se and was described for example in the work "Chromatographies en phases liquide et supercritique" by R. Rosset, M. Caude and A. Jardy, 1991, Masson S. A.

For example, a support of general formula (XI) schematized below:

(XI)

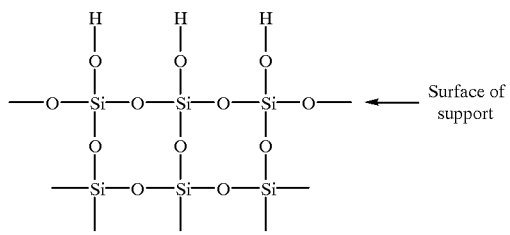

and where the formulae below schematize the reactive part of the support

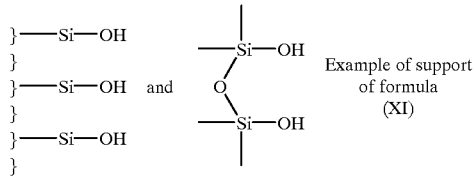 Example of support of formula (XI)

and a compound containing a radical of general formula (II), and which can, also in order to simplify the presentation of reaction diagrams, be symbolized by a radical of general formula:

$(X)_3Si\text{—}R\text{—}$ (XIa)

where R represents the radical:

(XIb)

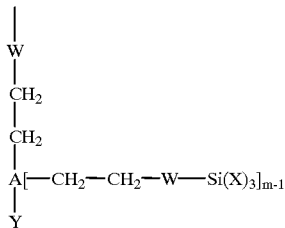

The employment of the support and compounds $(X)_3Si\text{—}R\text{—}$ leads to the following series of reactions:

a) Case where X=—OH or alkoxy (IXaa)

traces of water ⟶

(XII)

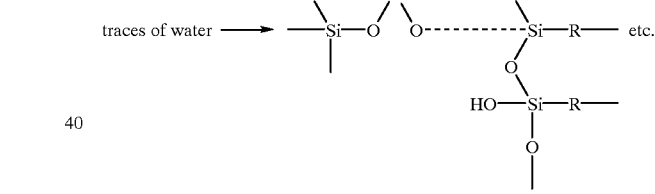

(IXa)

traces of water ⟶ b) Case where X=chlorine

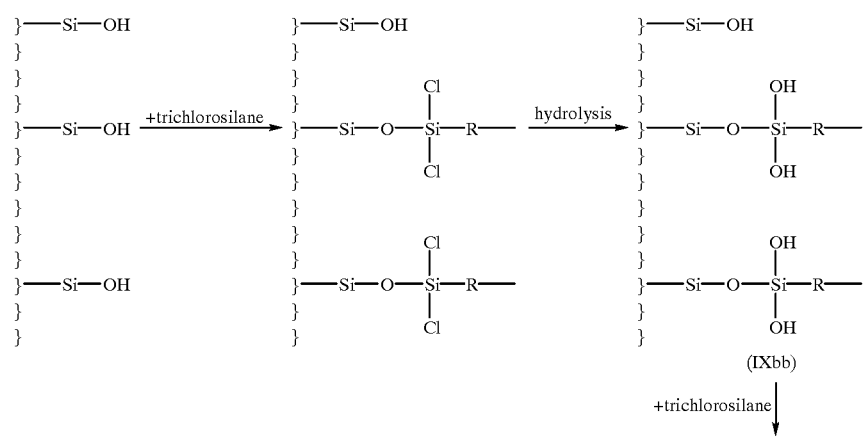

(IXbb)

+trichlorosilane ↓

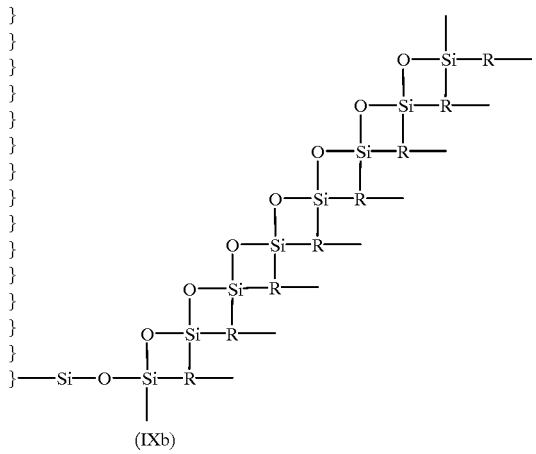

(IXb)

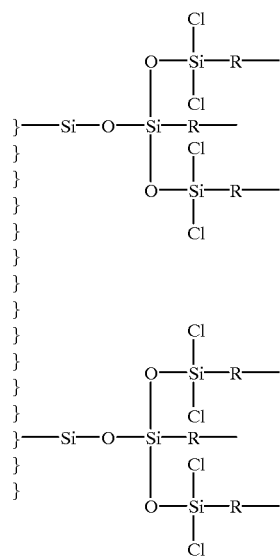

The symbol

CHIRAL UNIT of formulae (IX), (IXc) and (IXd) both represents a compound of formula (Ia) to (Ik) and schematizes a chiral osidic unit of an osidic linkage of a silane derivative of a polysaccharide.

The support materials have a complex structure as they are three-dimensional. They can be represented by the set of general formulae (IXaa), (IXa), (IXbb), (IXb), (IXc), (IXd), (XII), (XIII) and (XIV).

The compounds of general formula (IX) represent one of the possible combinations:

reaction with the support leading to compounds of formulae (XII) when m=1;
and concomitant reaction leading to compounds of formula (XIII) when m=1, i.e. formula (IXc), m having the same meaning as in formula (II).

In reality there are a significant number of possible combinations for the compounds of general formulae (IXaa), (IXa), (IXbb), (IXb) and (XII).

The employment of chlorosilanes, hydroxysilanes and alkoxysilanes of polysaccharides on supports leads to compounds of general formula (IX).

The supports used can be silica gel, alumina, zirconia, titanium oxide or magnesium oxide.

Concomitantly to the reactions described previously and resulting in the formation of compounds of general formula (IXaa), (IXa), (IXbb), (IXb) and (XII), a cross-linking reaction occurs between the chains of the silane derivatives of polysaccharides of formulae (Ia) to (Ik). In fact, this reaction takes place simultaneously as the chemical functions employed, chlorosilanes, hydroxysilanes and alkoxysilanes, are strictly identical to those previously employed with the support.

In fact, an interchain cross-linking occurs with the silane derivative of polysaccharide leading to the formation of a three-dimensional network by the creation of bonds:

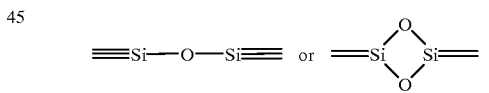

The principle of the cross-linking by reaction of silanes contained on two different chains of the silane derivative of polysaccharide is schematized in the reaction below:

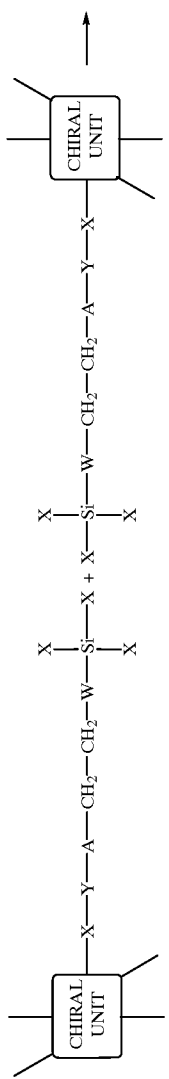
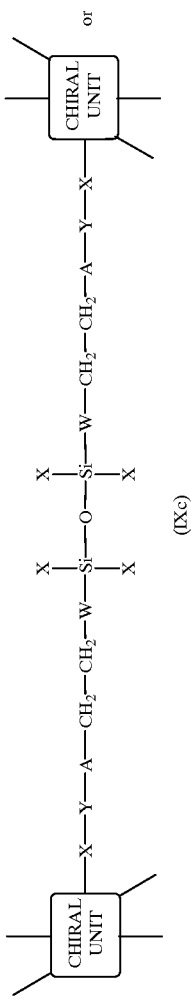
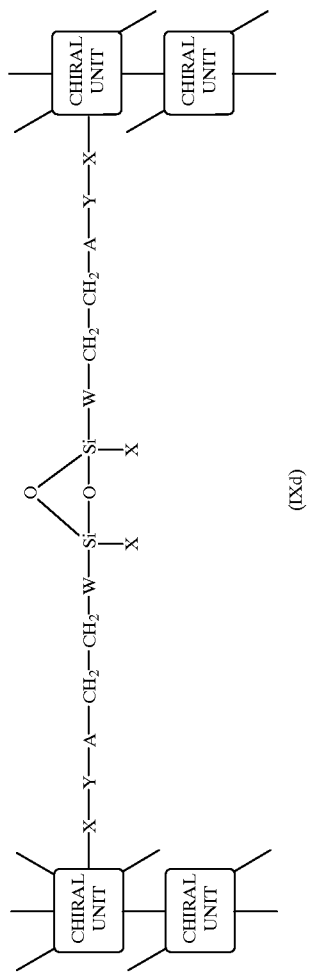

-continued
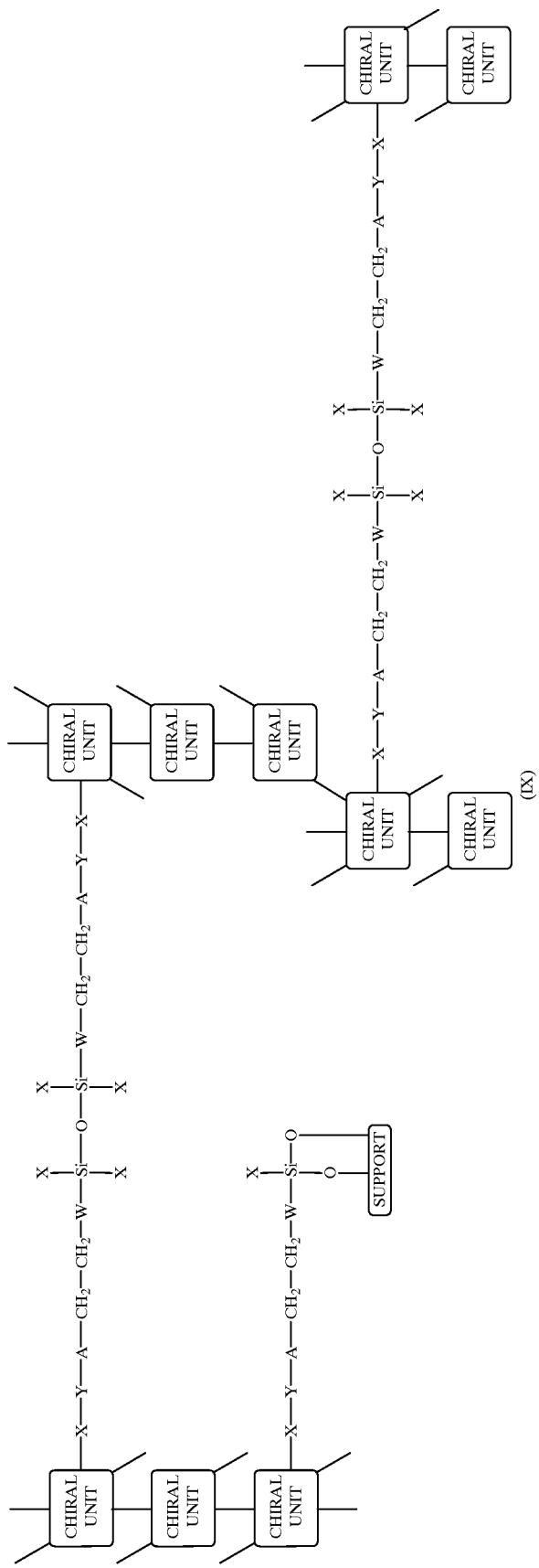
(IX)

where "support" represents a compound of general formula

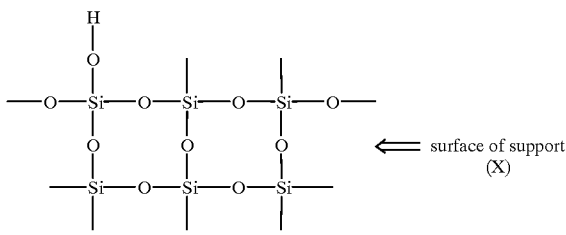

⇐ surface of support (X)

with Si representing the silicon or titanium or zirconium or aluminium or magnesium atom;
where W, A, Y and X are as defined previously in formulae (Ia) to (Ik);
and where "chiral unit" represents a compound of formula (Ia) to (Ik).

The invention also relates to a method for obtaining support materials which comprises:
physically depositing a silane derivative of polysaccharide of general formula (Ia) to (ik) on a support of general formula:

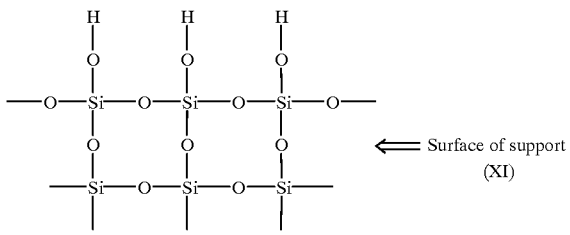

⇐ Surface of support (XI)

where Si has the same meaning as in formula (X):
and reacting the silanes represented in the radical of formula (II) according to two principle reaction methods (a) and (b):
a) reaction with a support of formula (X) to lead to the compounds of general formula (IXaa), (IXa), (IXbb), (IXb), (XII) and (IX);
b) cross-linking said silanes between themselves to lead to compounds of general formula (IXc), (IXd), (XIII) and (XIV).

Formula (IXc) corresponds to formula (XIII) for m=1
Formula (IXd) corresponds to formula (XIV) for m=1,
m having the same meaning as in formula (II).

The two reaction methods (a) and (b) are carried out simultaneously and allow the bonding of the silane derivative of polysaccharide by a covalent bond onto the support and polymerizing and cross-linking said silane derivatives of polysaccharides in a three-dimensional network.

Surprisingly, the support materials obtained possess a remarkable stability in all organic solvents, and more particularly in polar organic solvents having a high dissolving power for benzoate and carbamate derivatives of polysaccharides, such as chloroform, acetone, tetrahydrofuran, dioxan or toluene.

Equally surprisingly, these support materials are stable in the solvents mentioned previously up to temperatures of 80° C. or more. For example, a test for selectivity ($\alpha$) carried out on 2,2,2-trifluoro-1(9-anthryl)ethanol with a support material synthesized according to Example 1 showed that the selectivity factor $\alpha$ ($\alpha$=1.54 in chloroform) obtained according to Example 1, is not affected by the passage of some 1000 dead column volumes of the following solvents:

| Solvents | Conditions | Solvents | Conditions |
| --- | --- | --- | --- |
| Diisopropyl ether | from 20 to 80° C. | Propionitrile | 40° C. |
| Diethyl ether | 60° C. | Benzene | 80° C. |
| Dibutyl ether | 40° C. | Butyl chloride | 80° C. |
| Tert-butyl methyl ether | 60° C. | Chloroheptane | 80° C. |
| Acetaldehyde diethyl acetal | 40° C. | 1,1,1-trichloroethane | 40° C. |
| 1,4-dioxan | 40° C. | Dichloro 1,2-ethane | 40° C. |
| Ethylene glycol dimethyl ether | 40° C. | Trifluoroethanol | 40° C. |
| 2-methoxy ethyl ether | 40° C. | Tert-butyl hydroperoxide | 40° C. |
| Ethyl butyrate | 40° C. | Butyl acetate | 40° C. |
| Methanol | 40° C. | Ethanol | 40° C. |
| Isopropanol | 40° C. | 1-butanol | 40° C. |
| Acetonitrile | 40° C. | | |

These properties permit consideration of the use of support materials in processes for the separation or preparation of enantiomers using any type of polar solvent up to temperatures of at least 80° C., which seems particularly attractive for industrial applications.

The stability of the support materials was also evaluated by dissolution at reflux of the various solvents of the preceding table. Surprisingly the results show that the loss of mass of support material synthesized according to Example 1, is nil after hot filtration and drying. This result indicates that the silane derivative of polysaccharide of example 1 is indeed bound to the support by a covalent bond and that the creation of Si—O—Si— bonds has occurred between the chains of the silane derivative of polysaccharide, the cross-linking obtained having concerned all of the structure of the silane derivative of polysaccharide. In fact, the silane derivatives of polysaccharides of formulae (Ia) to (Ik) are soluble in polar organic solvents such as those mentioned in the preceding table, cold and hot. (Furthermore, this property is used to realize the physical deposit of the compounds of formula (Ia) to (Ik) on a support). The loss of mass of the support material being nil, it can be estimated that compounds of the chemical structure represented by formulae (Ia) to (Ik) no longer exist in said support materials, which indicates that the totality of the compounds of formula (Ia) to (Ik) were transformed into support material of general formula (IX).

The physical deposit of a derivative of polysaccharide of general formula (Ia) to (Ik) on a support is realized according to two techniques:
evaporation of a solution of said derivatives of polysaccharides at normal pressure or under vacuum, in the presence of a support; or
precipitation by addition of a solvent in which said derivatives of polysaccharides are insoluble, in the presence of a support.

Generally, said derivatives of polysaccharides are solubilized in polar organic solvents such as chloroform, dichloromethane, acetone, dioxan, pyridine, tetrahydrofuran or toluene. A support of general formula (XI) with a granulometry of 0.1 $\mu$m to 1 mm and with a pore diameter of 10 Å to 10000 Å is added to this solution of derivatives of polysaccharides, the preferred support being silica gel.

The quantity of polysaccharide varies from 1 to 70% by weight relative to the mass of support added. A suspension is obtained.

If the technique by evaporation is chosen, the suspension obtained previously is dried by distillation of the solvent at normal pressure or under vacuum. A product is obtained which is constituted by a support on which a silane derivative of polysaccharide of formula (Ia) to (Ik) is physically deposited. This product is called composite.

If the technique by precipitation is chosen, a solvent in which the derivative of polysaccharide is insoluble is added to the suspension obtained previously, hexane or heptane being the preferred solvents. The suspension is filtered, washed with heptane and dried at 40° C. under vacuum. A product is obtained of the same nature as that obtained in the technique by evaporation. This product is also called composite.

The composite thus obtained is suspended in a solvent in which the derivative of polysaccharide is insoluble, the preferred solvents being heptane or hexane, and the suspension is taken to reflux for, for example, twelve hours. The supply of calories allows the chlorosilanes, hydroxysilanes and alkoxysilanes contained in the silane derivatives of polysaccharides, to enter into reaction with the silanol groups contained in the surface of the silica gel support. The grafting reaction of the chlorosilanes, hydroxysilanes and alkoxysilanes on the silica gel supports containing silanols is known per se and was described in several works such as "Silica Gel and Bonded Phases", R. P. W. Scott, 1993, Separation Science Series, R. P. W. Scott and C. F. Simpson editors, John Wiley & Sons Ltd. The use of chlorosilanes leads to the formation of hydrochloric acid and trapping this takes place by the use of a base such as pyridine. The use of hydroxysilane leads to the formation of water. The use of alkoxysilanes leads to the formation of the corresponding alcohols (methanol for methoxysilane and ethanol for ethoxysilane). These different grafting reactions lead to the formation of a chemical covalent bond with the support of the same chemical nature [—Si—O-(Support)].

The polymerization of chlorosilanes, hydroxysilanes and alkoxysilanes is known per se and was described in "Silica Gel and Bonded Phases", R. P. W. Scott, 1993, Separation Science Series, R. P. W. Scott and C. F. Simpson editors, John Wiley & Sons Ltd.

The polymerization of chlorosilanes takes place in the presence of traces of water; hydroxysilanes polymerize by forming water and alkoxysilanes polymerize by releasing the corresponding alcohol (methanol for methoxysilanes and ethanol for ethoxysilanes). These different polymerization reactions lead to the realization of covalent bonds of the same chemical nature: Si—O—Si (the siloxane bond or siloxane graft). By only taking into account, at the level of the composite, the reactive chemical parts, namely the support and the radical of formula (II) contained in the derivatives of polysaccharides (Ia) to (Ik), the balance of the two concomitant chemical reactions employed to synthesize the support material from the composite is the following:

reaction with the support

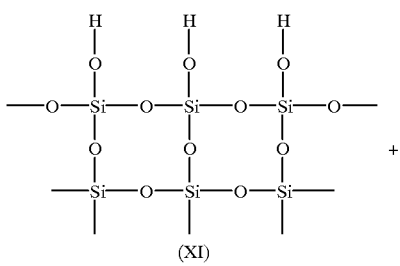

(XI)

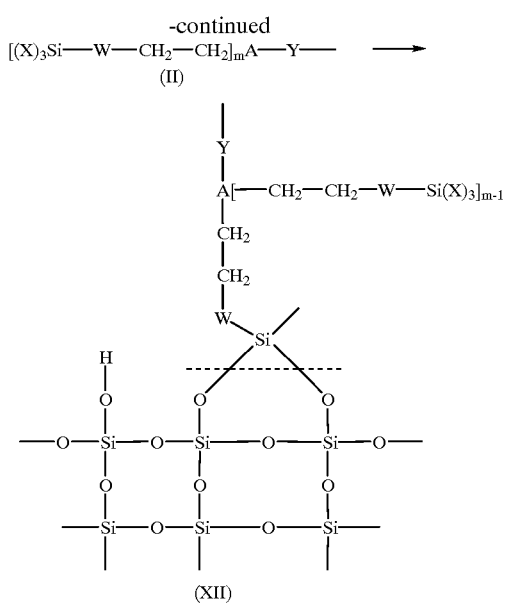

(XII)

In order to avoid too great a complexity in the figure representing the support material of general formula (IX), the radical part $[CH_2—CH_2—W—Si(X)_3]_{m-1}$ is not shown, it having not reacted.

Although not represented in formula (IX), the radical part above can obviously enter into the reaction and particularly in the reaction concomitant to the previous reaction "reaction with the support" and which is called "cross-linking". In this case the radical part m−1 is involved and leads to a reaction product of order m−2 and so on.

Cross-linking:

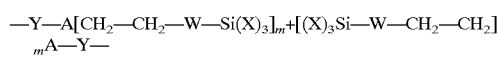

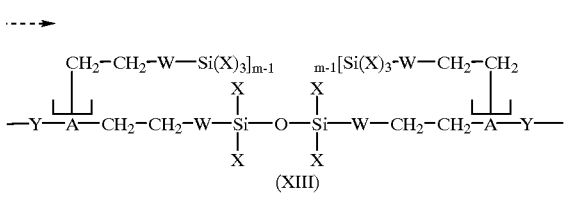

and/or

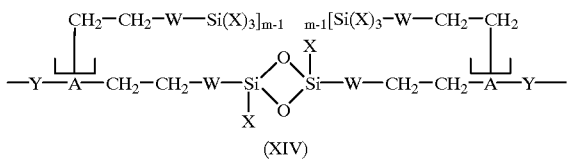

In formulae (XIII) and (XIV), as in the case of the compounds of formulae (XII), the radical part $[—CH_2—CH_2—W—Si(X)_3]_{m-1}$ can concomitantly react in order to lead to a new covalent bond of order m−2, which can itself lead to a bond of order m−3 and so on.

The invention also relates to methods for using said support materials in separation or in preparation of enantiomers by employing in:

gas chromatography liquid chromatography, from −10° C. to +80° C., in particular in pure polar organic solvents such as those mentioned in the table below

| Solvents | Solvents |
|---|---|
| Diisopropyl ether | Propionitrile |
| Diethyl ether | Benzene |
| Dibutyl ether | Butyl chloride |
| Tert-butyl methyl ether | Chloroheptane |
| Acetaldehyde diethyl acetal | 1,1,1-trichloroethane |
| 1,4-dioxan | Dichloro 1,2-ethane |
| Ethylene glycol dimethyl ether | Trifluoroethanol |
| 2-methoxy ethyl ether | Tert-butyl hydroperoxide |
| Ethyl butyrate | Butyl acetate |
| Methanol | Ethanol |
| isopropanol | 1-butanol |
| Acetonitrile | Dichloromethane |
| Chloroform | Carbon tetrachloride |
| Dichloroethane | Ethyl acetate |
| Methyl acetate | Dichlorobenzenes |
| Xylenes | Dimethyl sulphoxide |
| Trichloroethane | Dimethyl formamide |
| Tetrahydrofuran | |

In hydro-organic, aqueous or organic mixtures, under isocratic conditions or in gradient mode:

supercritical chromatography electrophoresis or electrochromatography percolation through membranes constituted by said support materials organic synthesis in heterogeneous medium.

The following examples illustrate the present invention but in no way limit it.

EXAMPLE 1

0.5 g of native cellulose (marketed by the company Merck), containing 3.1 mM of glucose units, is suspended in 15 cm$^3$ of toluene. After dehydration of the cellulose by azeotropic distillation until dry, 40 cm$^3$ of pyridine are added. After distillation of 15 cm$^3$ of solvent and cooling, 1.32 g of 10-undecenoyl chloride (6.5 mM) are added. The mixture is heated under reflux for 1 hour and a sample is taken, the elemental analysis of which (C=67.55%; H=9.27%) shows that the degree of substitution is 1.8. 0.850 g of 3,5-dimethyl phenyl isocyanate (5.6 mM) is then added and the mixture is heated under reflux for a night. After hot filtration over no. 2 fritted glass, the reaction mixture is poured into 100 cm$^3$ of methanol. After filtration, the precipitate is dissolved in the minimum of pyridine. The solution is filtered over no. 2 fritted glass and the filtrate is poured into an ethanol/water mixture (1/1 by volume). After filtration and washing with methanol, a product with the following characteristics is obtained:

elemental analysis: C=68.58%; H=8.67%; N=2.12%.

degree of substitution: 1.8 (undecenoyl), 0.9 (3,5-dimethyl-phenyl carbamate).

A compound of general formula (Id) is obtained

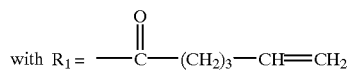

-continued

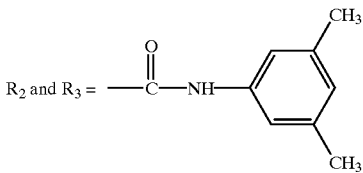

and

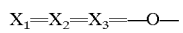

This compound is given the reference Id-E1.

0.3 g of the previous compound are solubilized in solution in 50 ml of chloroform. 70 µl of 3-mercaptopropyltrimethoxysilane are added, as well as 30 mg of azo-isobutyronitile. The reaction medium is taken to reflux for 6 hours. The reaction medium is precipitated from 200 ml of chloroform and the suspension is filtered, then dried at 40° C. under vacuum. The dry product is solubilized in 20 ml of toluene and 20 ml of pyridine and 4 g of silica gel 5 µm (particle diameter), 200 Å (pore diameter) are added. The suspension is taken to reflux for 48 hours and the solvent is evaporated off under vacuum at 80° C.

The solid is dried at 60° C. under vacuum, then ground. It is taken up in 50 ml of tetrahydrofuran for 3 hours then filtered. It is dried again at 60° C. under vacuum. An HPLC column is filled with this support and the column is inserted into an HPLC assembly. The efficacy of this support as a separation medium was then tested using a racemic mixture of 2,2,2-trifluoro-1-(9-anthryl)ethanol.

A 250×4.6 mm HPLC column

Solute: 2,2,2,-trifluoro-1-(9-anthryl)ethanol

Mobile phase: pure chloroform

Flow rate: 1 ml/mm–O.D.=0.01–temperature 25° C.–λ=254 nm k'1=3.14–k'2=4.83–α=1.54 are obtained

EXAMPLE 2

0.3 g of the compound reference Id-E1 of Example 1 are solubilized in 30 ml of tetrahydrofuran. 0.1 ml of triethoxysilane are added, 0.05 g of hexachloroplatinic acid are added. The solution obtained is taken to reflux for 48 hours. The reaction mixture is cooled, then poured into 300 ml of methanol. The suspension obtained is filtered then dried at 40° C. under vacuum. The dry product is again solubilized in 40 ml of pyridine and 4 g of silica gel, particle diameter 5 µm and porosity 200 Å are added.

The reaction suspension is taken to reflux for 48 hours, then the pyridine is evaporated to dryness. The solid is dried at 80° C. under vacuum. It is then taken up in 50 ml of tetrahydrofuran for three hours then filtered. It is again dried at 60° C. under vacuum.

An HPLC column is filled with this support and the column is inserted in an HPLC assembly. The efficacy of this support as a separation medium was then tested using a racemic mixture of 1,1'-bi-2-naphthol.

A 250×4.6 mm HPLC column

Solute: 1,1,-binaphthol

Mobile phase: pure chlorobutane

Flow rate: 1 ml/mm–O.D.=0.01–λ=254 nm k'1=3.00–k'2=4.43–α=1.48

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/11,377, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Derivative of chlorosilane, hydroxysilane or alkoxysilane type of polysaccharides or oligosaccharides, constituted by linear, branched or cyclic linkages of osidic chiral units and represented by one of the following formulae (Ia) to (Ik):

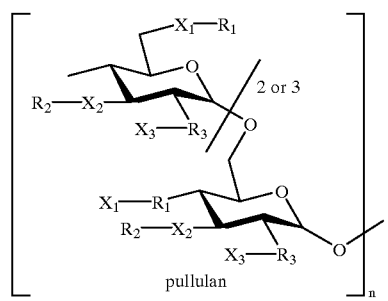
Ia pullulan

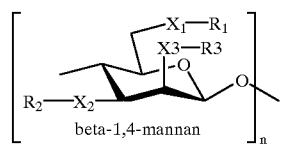
Ib beta-1,4-mannan

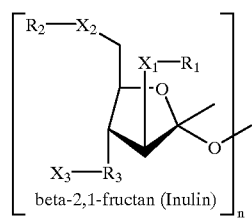
Ic beta-2,1-fructan (Inulin)

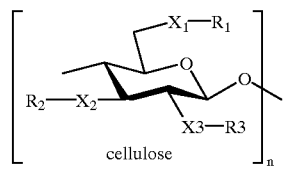
Id cellulose

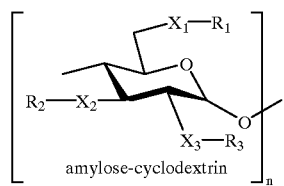
Ie amylose-cyclodextrin

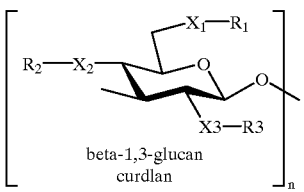
If beta-1,3-glucan curdlan

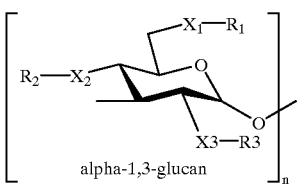
Ig alpha-1,3-glucan

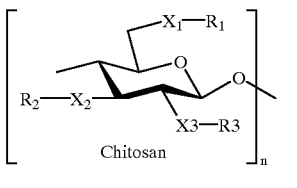
Ih Chitosan

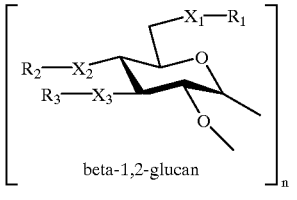
Ii beta-1,2-glucan

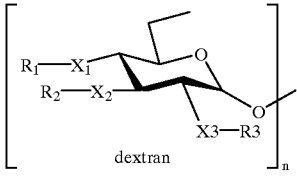
Ij dextran

Ik beta-1,4-xylan in which:
a) the symbols $X_1$, $X_2$ and $X_3$, identical or different, each represent an oxygen atom or the —NH group;
b) each of the symbols $R_1$, $R_2$ and $R_3$ independently represents:
a chlorosilane, hydroxysilane or alkoxysilane radical of general formula $[(X)_3Si$—W—$CH_2$—$CH_2]_m$A—Y— (II) in which m is a non-zero integer at most equal to 5, Y is a single bond, an —NH—CO— group, an —NH—CS— group or a —CO— group, A represents an arylene radical having 6 to 18 atoms or an aralkylene radical having 7 to 40 carbon atoms, W represents a single bond or the —$CH_2$—$CH_2$—$CH_2$—S— group and X represents a halogen, a hydroxyl or an alkoxy;
or a radical having the formula $A_2$—$A_1$—$CX_4$— (III) in which $X_4$ represents an oxygen or sulphur atom, $A_1$ represents a single bond or an —NH— group and $A_2$ represents an aryl radical having from 6 to 24 carbon atoms, an aralkyl radical having from 7 to 36 carbon atoms or an alkylaryl radical having from 7 to 18 carbon atoms;

or a hydrogen atom or an $NO_2$ group, n being an integer between 5 and 20,000, it being understood that, in each osidic chiral unit (Ia) to (Ik), at least one of the symbols $X_1$, $X_2$ and $X_3$ represents an oxygen atom, and that, in at least one part of the structural units constituting the polysaccharide, at least one of the symbols $R_1$, $R_2$ and $R_3$ represents a radical of general formula (II) and at least one of the symbols $R_1$, $R_2$ and $R_3$ represents a radical of general formula (III).

2. A silane derivative of polysaccharide according to claim 1, characterized in that the aryl radicals $A_2$ in general formulae III are phenyl or naphthyl radicals and/or the arylene radicals A and $A_1$, in general formulae II and III are phenylene or naphthylene radicals.

3. A silane derivative of polysaccharide according to claim 2, in which the arylene or aryl radicals contained respectively in the radicals of general formulae (II) and (III) are substituted by one or more atoms or radicals, identical or different, chosen from halogen atoms, alkyl radicals containing from 1 to 4 carbon atoms, alkoxy radicals containing from 1 to 4 carbon atoms and nitro groups.

4. Support material according to claim 1 characterized in that the silane derivative of polysaccharide of formulae Ia) to (Ik) which contain it is polymerized or cross-linked in a three-dimensional network by the formation of the following bonds:

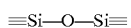

or

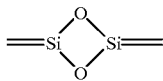

5. Support material according to claim 1 characterized in that the silane derivative of polysaccharide is both bound to the support by a chemical covalent bond and polymerized or cross-linked in a three-dimensional network.

6. Polymerized compound represented by one of general formulae (IXaa), (IXa), (IXbb), (Ixb) and (XII) of the description, and wherein A represents an arylene radical having 6 to 18 carbon atoms or an aralkylene radical having 7 to 40 carbon atoms.

7. A cross-linked compound represented by one of general formulae (IXc), (IXd), (XIII) and (XIV):

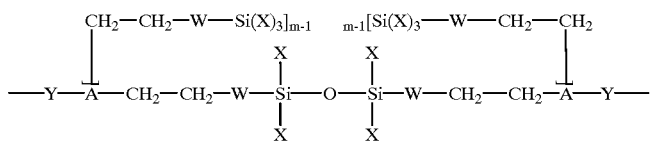

(XIII)

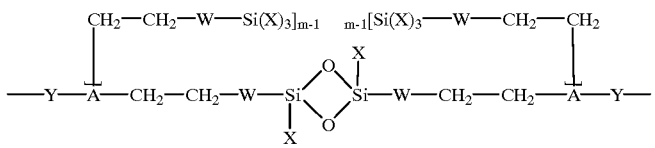

(XIV)

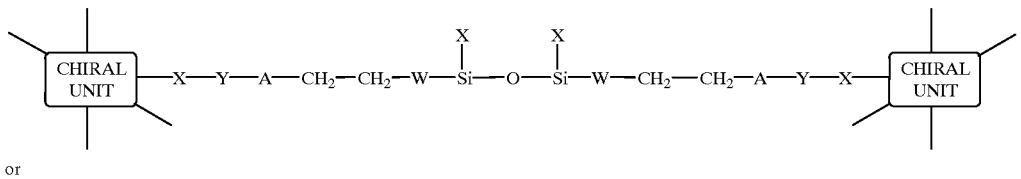

(IXc)

or

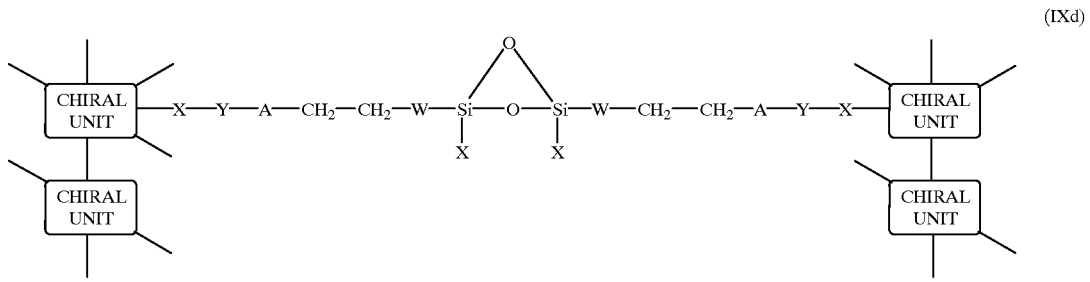

(IXd)

formula (IXc) corresponds to formula (XIII) for m=1, formula (IXd) corresponds to formula (XIV) for m=1, and Y, A, W, X and m having the same meaning as in formula (II).

8. A cross linked compound according to claim 7, wherein A represents an arylene radical having 6 to 18 carbon atoms or an aralkylene radical having 7 to 40 carbon atoms.

9. Support material having covalent bonds —Si—O—(Support)-, said support materials being represented by the combination of general formulae (IXaa), (IXa), (IXbb), (IXb), (IXc), (IXd), (XII), (XIII) and (XIV), where "chiral unit" corresponds to one of the osidic chiral units contained in the polysaccharide linkage represented by general formulae (Ia) to (Ik).

10. Support material according to claim 9 characterized in that it is represented by general formula (IX), combination of formula (XII) and formula (IXc) for m=1, m having the same meaning as in formula (II):

(IX)
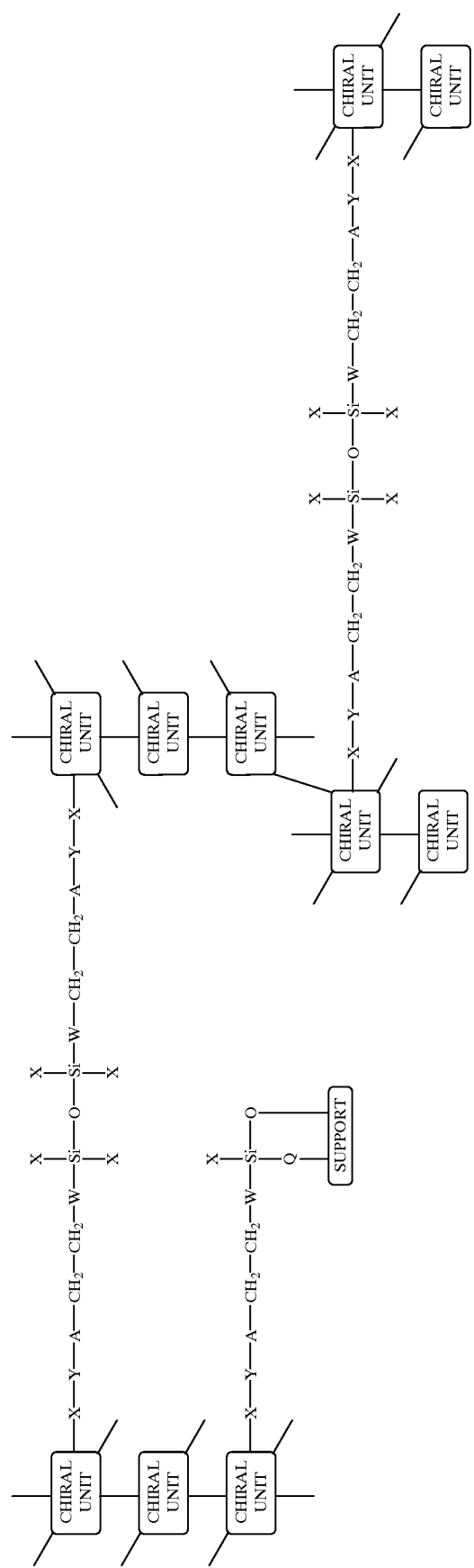

11. Support material according to claim 9 characterized in that it contains at least one compound of general formula (IXaa), (IXa), (IXbb), (IXb) or (XII).

12. Support material according to claim 9 in the form of a three-dimensional network characterized in, that it contains at least one compound of general formula (IXc), (IXd) (XIII) or (XIV).

13. Support material according to claim 9 characterized in that the support carrying covalent bonds is represented by the following general formula:

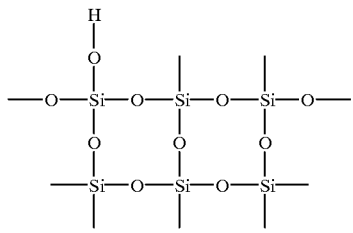

(X)

where Si represents the silicon, titanium, zirconium, aluminium or magnesium atom.

14. Support material according to claim 9 characterized in that its granulometry is comprised between 0.1 $\mu$m and 1 mm and its porosity between 0.1 $m^2/g$ and 800 $m^2/g$.

15. Method for obtaining a support material according to claim 9 characterized in that a silane derivative of polysaccharide is deposited on a support and then said silane derivative of polysaccharide is reacted with the support and in a concomitant fashion with itself in order to create covalent bonds between the silane derivative of polysaccharide and the support and to cross-link the silane derivative of polysaccharide and the support and to cross-link the silane derivative of polysaccharide in a three-dimensional network, said method comprising:

physically depositing a silane derivative of polysaccharide of general formula (Ia) to (Ik) on a support of general formula:

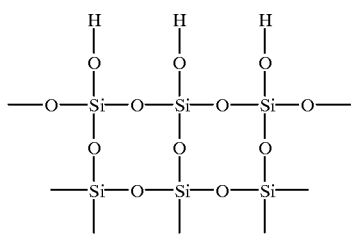

(XI)

where Si has the same meaning as in formula (X): and implementing two reaction methods consisting of:
reaction of the silane radicals of general formula (II) with the support, of general formula (XI), to lead to the compounds of general formula (IXaa), (IXa), (IXbb), (IXb), and (XII):

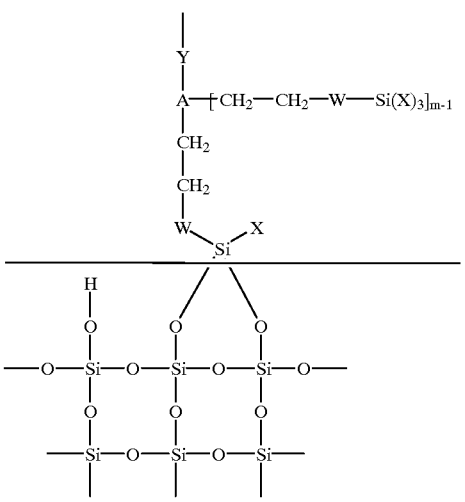

and/or reaction of the silane radicals of general formula (II) on themselves in order to lead to compounds of general formula (IXc), (IXd), (XII) and (XIV).

16. In preparing or separating enantiomers with means of liquid or gaseous or supercritical chromatography, or means of electrophoresis or electrochromatography, the improvement wherein said means comprises a support material according to claim 9.

17. A percolation membrane comprising a support material according to claim 9.

18. A process comprising conducting an organic synthesis in heterogeneous phase, wherein the heterogeneous phase comprises a support material according to claim 9.

19. A support material according to claim 9, wherein A represents an arylene radical having 6 to 18 carbon atoms or an aralkylene radical having 7 to 40 carbon atoms.

20. A process for the production of the silane derivatives of claim 1, wherein a reaction is carried out successively on a polysaccharide:

in stage 1, of a compound of general formula:

(IV)

in which R, m and A are defined as previously and $Y_1$ represents a halogen atom, an —N═C═O group or —N═C═S group or a —CO—Z— group in which Z represents a halogen atom in order to introduce an ethylene radical, subsequently modified in stage 3 into chlorosilane, hydroxysilane or alkoxysilane;

in an optional stage 2, an isocyanate or an isothiocyanate of general formula:

(V)

in which $A_2$ and $A_1$ are defined as previously and $X_5$ represents an oxygen or sulphur atom or a compound of general formula:

(VI)

in which $A_2$ and $A_1$ are defined as previously and $Z_1$ represents a halogen atom in order to introduce a radical of general formula (III);

and, in stage 3, a compound of general formula:
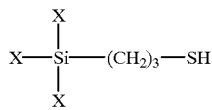
(VII)
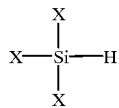
(VIII)
in which X is defined as previously in order to introduce a compound of general formula (II).
21. A process according to claim 20, comprising conducting optional stage 2.
22. A process according to claim 20, wherein A represents an arylene radical having 6 to 18 carbon atoms or an aralkylene radical having 7 to 40 carbon atoms.
* * * * *

UNITED STATES PATENT AND TRADEMARK OFFICE
CERTIFICATE OF CORRECTION

PATENT NO. : 6,346,616 B1
DATED : February 12, 2002
INVENTOR(S) : Duval

It is certified that error appears in the above-identified patent and that said Letters Patent is hereby corrected as shown below:

<u>Column 23,</u>
Line 18, delete "Derivative" and insert -- A derivative --.

Signed and Sealed this

Thirty-first Day of December, 2002

JAMES E. ROGAN
*Director of the United States Patent and Trademark Office*